United States Patent [19]

Adinolfi

[11] Patent Number: 5,152,031
[45] Date of Patent: Oct. 6, 1992

[54] NON-CONTAMINATING HANDLER

[76] Inventor: Raphael A. Adinolfi, 515-72 St., Brooklyn, N.Y. 11209

[21] Appl. No.: 345,971

[22] Filed: May 1, 1989

[51] Int. Cl.⁵ .................. A47B 95/02; A45F 5/00; A45F 3/14; B66C 1/04
[52] U.S. Cl. .................. 16/114 R; 16/124; 224/183; 224/219; 294/65.5
[58] Field of Search .............. 294/25, 65.5; 16/114 R, 16/124; 224/183, 219, 221

[56] References Cited

U.S. PATENT DOCUMENTS

| | | | |
|---|---|---|---|
| 2,164,623 | 7/1939 | Posner | 224/219 |
| 2,176,052 | 10/1939 | Beyer | 294/65.5 |
| 2,440,170 | 4/1948 | Duefrene | 16/114 R |
| 2,824,681 | 2/1958 | Sorkin | 224/183 |
| 2,976,075 | 3/1961 | Budreck | 294/65.5 |
| 3,302,566 | 2/1967 | Blanchet | 16/114 R |
| 4,325,504 | 4/1982 | Amani | 224/183 |
| 5,070,563 | 12/1991 | Tervola | 294/65.5 |

FOREIGN PATENT DOCUMENTS 2234634  1/1975  France ............. 224/219

Primary Examiner—John Sipos
Assistant Examiner—Carmine Cuda

[57] ABSTRACT

A device to allow health practitioners' cabinet drawers to be opened and operating lights and other moveable operating equipment to be repositioned as he works, without the need to grasp, and thereby contaminate, their handles. The device comprises magnet devices attached to the drawers and equipment and a wristband containing a piece of soft iron for contacting the attached magnet devices and moving the drawers and equipment without using the fingers.

5 Claims, 2 Drawing Sheets

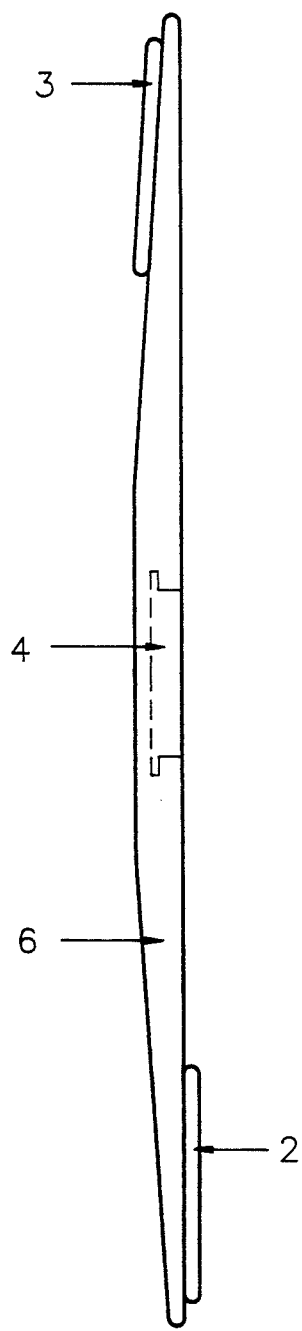
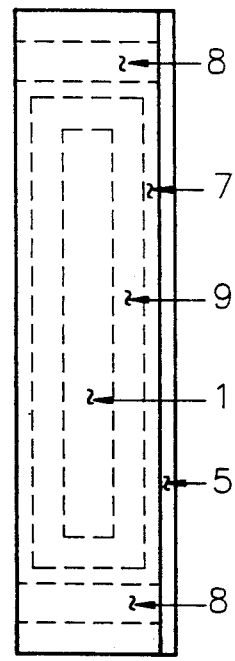
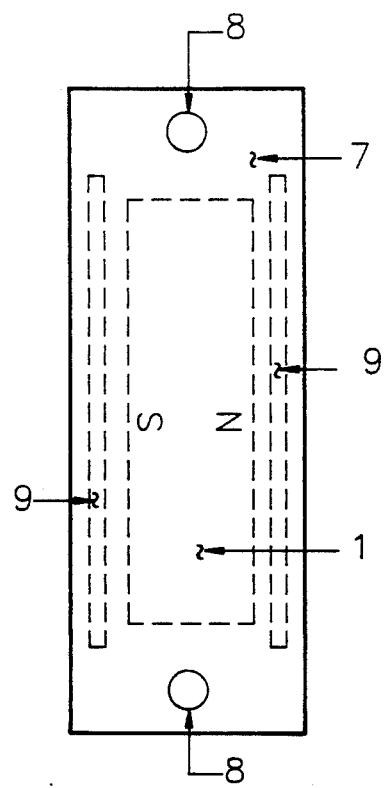
FIG. 1
FIG. 2
FIG. 3

NON-CONTAMINATING HANDLER

BACKGROUND OF THE INVENTION

1. Field of the Invention

The invention relates generally to magnetic bars, attached to the handles of health practitioners' equipment and cabinet drawers, that when contacted by a piece of soft iron embedded in a wristband worn by the health practitioner, will permit repositioning of the said equipment and opening of drawers without contamination of the fingers of the hands.

2. Description of the Prior Art

Currently in a dental operatory, all equipment and furniture handled or touched during each procedure must be sterilized, or at least disinfected, after each patient. This can be very time-consuming because the hands, whether gloved or ungloved, are involved in contact with infected areas and with the patients' body fluids, including saliva and blood, This invention would eliminate the need for disinfection of such items as cabinet drawer handles, the operating light, and other moveable operating equipment because they would no longer have to be gripped by contaminating fingers.

SUMMARY OF THE INVENTION

The invention relates to a device to allow health practitioners' cabinet drawers to be opened and operating lights and the other moveable operating equipment to be repositioned as he works, without the need to grasp their handles with one's fingers. It comprises a means for magnetically engaging various items and moving them, without the use of contaminated fingers.

It is comprised of a magnetic bar embedded in plastic, which attaches to items that are to be manipulated when engaged by a piece of soft iron embedded in a wristband, which is worn by the health practitioner.

It is an object of the invention to provide a device for manipulating operatory drawers, lights, and other moveable equipment during procedures without touching and contaminating their handles, thereby decreasing the amount of time needed to disinfect the equipment between patients.

BRIEF DESCRIPTION OF THE DRAWINGS

FIG. 1 is a side view showing the wristband of the Non-Contaminating Handler.

FIG. 2 is a top view showing the magnetic handling attachment of the Non-Contaminating Handler.

FIG. 3 is a plan view showing the magnetic handling attachment of the Non-Contaminating Handler.

DESCRIPTION OF THE PREFERRED EMBODIMENT

Figure 4:
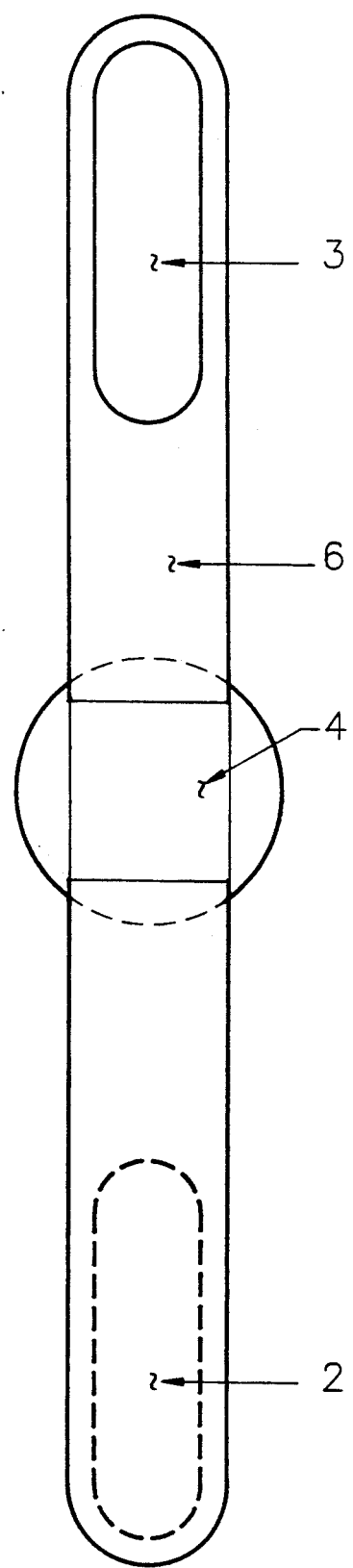
FIG. 4 is a plan view showing the wristband of the Non-Contaminating Handler.

Referring to FIGS. 1, 2, 3, and 4 an embodiment of the Non-Contaminating Handler is shown. In this embodiment, a magnet 1, embedded in an encasement 7 and a wristband 6 are shown. The magnet 1 is embedded in an encasement 7 and is encompassed on two sides by steel pole pieces 9, placed so as to position the magnetic field for maximum attaching effect. The encasement 7 may be constructed of any material and the invention relates to any configuration of the encasement 7. The encasement 7, containing the magnet 1 and the pole pieces 9, is attached to cabinetry and other moveable operating equipment in a health practitioners' operatory. Any means for attaching the magnetic handling attachment to the equipment may be used, including self-adhesive backing 5, hardware placed through holes 8 provided, or other means.

Referring to FIGS. 1 and 4, a representation of the wristband worn by the health practitioner is shown. A piece of soft iron 4 is embedded in the wristband 6. It is held on the wrist by any means of attachment, including a rough Velcro fastener 3 being contacted by a smooth Velcor fastener 2, snap fasteners, a buckle, or other means.

The handling attachment shown in FIG. 3 is attached to cabinet drawers, the operating light, or other moveable operating equipment. To open a drawer or reposition equipment during a procedure, the health practitioner touches the wristband 6 to the handling attachment. The drawers and other equipment may then be moved without touching, and thereby contaminating them with the fingers. The invention minimizes the standard practice of having to disinfect, after each patient, all drawer handles and handles of all equipment touched during a procedure.

Although one detailed embodiment of the invention is illustrated in the drawings and previously described in detail, the invention contemplates any configuration, design, and relationship of components which will function in a similar manner and which will provide the equivalent result.

I claim:

1. A device for opening cabinet drawers and repositioning operating equipment without touching and thereby contaminating their handles, which comprises:
   (a) a plurality of magnet mans, each magnet means comprising a magnet embedded in an encasement, and which are attached to said cabinet drawers and to the handles of said other moveable operating equipment; and
   (b) a wristband containing a piece of soft iron, which is worn on the wrist of a health practitioner for contacting said magnet mans for opening said drawers and moving said equipment without hand contact; said magnet means having a sufficient attracting force on said soft iron to move said drawers and said equipment by the wristband.

2. A non-contaminating handling device as recited in claim 1, in which the magnet is encompassed on two sides by steel pole pieces, placed so as to position the magnetic field for maximum attaching effect.

3. A non-contaminating handling device as recited in claim 2, in which each of said magnet means has a means for attachment to cabinetry and to the handles of moveable operating equipment.

4. A non-contaminating handling device as recited in claim 3, in which the wristband has a means for attachment around the wrist of the health practitioner.

5. A non-contaminating handling device as recited in claim 4, in which both the wristband and the magnet means are made of a material which will provide them with smooth, disinfectable surfaces.

* * * * *